(12) United States Patent
Ali

(10) Patent No.: US 12,702,738 B2
(45) Date of Patent: Aug. 11, 2026

(54) SYSTEM AND METHODS INCORPORATING REPLACEMENT FLUID MAXIMIZATION

(71) Applicant: Fenwal, Inc., Lake Zurich, IL (US)

(72) Inventor: Zahra R. Ali, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 526 days.

(21) Appl. No.: 18/315,208

(22) Filed: May 10, 2023

(65) Prior Publication Data

US 2023/0270926 A1 Aug. 31, 2023

Related U.S. Application Data

(63) Continuation of application No. 16/854,519, filed on Apr. 21, 2020, now Pat. No. 11,679,188.
(Continued)

(51) Int. Cl.
*A61M 1/34* (2006.01)
*A61M 1/00* (2006.01)
(Continued)

(52) U.S. Cl.
CPC .......... *A61M 1/3496* (2013.01); *A61M 1/303* (2014.02); *A61M 1/304* (2014.02);
(Continued)

(58) Field of Classification Search
CPC .... A61M 1/3496; A61M 1/303; A61M 1/304; A61M 1/85; A61M 2202/0415;
(Continued)

(56) References Cited

U.S. PATENT DOCUMENTS 5,360,542 A 11/1994 Williamson, IV et al.
5,868,696 A 2/1999 Giesler et al.
(Continued)

FOREIGN PATENT DOCUMENTS

WO 2017140416 A2 8/2017

OTHER PUBLICATIONS

European Patent Office, Extended European Search Report, counterpart EP Appl. No. 20171056 (Sep. 23, 2020) (8 pages).

*Primary Examiner* — Jacqueline F Stephens
*Assistant Examiner* — Nhu Q. Tran
(74) *Attorney, Agent, or Firm* — Cook Alex Ltd.

(57) ABSTRACT

A processing system includes a processor including a separator, a set configured to cooperate with the separator to separate whole blood into plasma and other components, the set including an inlet line attachable to a patient to receive whole blood and an return line attachable to a patient to return processed fluid, and a source of replacement fluid connected to the disposable set, the processor configured to combine the other components with replacement fluid to define the processed fluid. The processor includes a controller and an input device coupled to the controller, the controller configured to receive an input via the input device, the input representing a volume of replacement fluid, and to control the processor to separate whole blood passing through the set and to combine the other components with the replacement fluid according to the input until the source of replacement fluid is empty.

16 Claims, 4 Drawing Sheets

Related U.S. Application Data

(60) Provisional application No. 62/837,509, filed on Apr. 23, 2019.

(51) Int. Cl.
*A61M 1/30* (2006.01)
*A61M 1/36* (2006.01)

(52) U.S. Cl.
CPC ............ *A61M 1/3622* (2022.05); *A61M 1/85* (2021.05); *A61M 2202/0415* (2013.01); *A61M 2205/50* (2013.01)

(58) Field of Classification Search
CPC ............ A61M 2205/50; A61M 1/3437; A61M 1/3693; A61M 2202/0474; A61M 2205/3379; A61M 1/38
See application file for complete search history.

(56) References Cited

U.S. PATENT DOCUMENTS

2008/0209357 A1* 8/2008 Vasta ...................... G16Z 99/00
715/771
2010/0168639 A1 7/2010 Cantu et al.
2010/0312039 A1* 12/2010 Quirico ............... A61M 5/1452
600/4
2013/0233394 A1* 9/2013 Nguyen .............. A61M 1/3496
137/395
2018/0344921 A1* 12/2018 Ragusa ................... A61M 1/38
2020/0147289 A1* 5/2020 Patel ..................... A61M 1/385
2020/0330673 A1* 10/2020 Breuel .................. A61M 5/445

* cited by examiner

SYSTEM AND METHODS INCORPORATING REPLACEMENT FLUID MAXIMIZATION

CROSS-REFERENCE TO RELATED APPLICATIONS

This application is a continuation of Ser. No. 16/854,519 filed Apr. 21, 2020, which claims the benefit of U.S. Provisional Patent App. No. 62/837,509, filed Apr. 23, 2019, all of which are expressly incorporated herein by reference in their entireties.

TECHNICAL FIELD

The present disclosure is generally directed to a system and method that may be used when replacing a blood component, such as plasma, with a replacement fluid, and in particular a blood processing system or method that maximizes the replacement fluid used during such a replacement procedure.

BACKGROUND

Blood processing systems may be used to process blood drawn from a patient, and then to return the processed fluid to the patient. These blood processing systems may include a reusable processor or separator, as well as a disposable fluid circuit or set that is connected to the patient. The set may also be connected to various containers that include other fluids, such as blood products, solutions and the like.

One procedure that is carried out using such a blood processing system is known as therapeutic plasma exchange, or TPE. In TPE, whole blood is removed from the patient, the plasma is exchanged for a designated replacement fluid, and the processed blood is returned to the patient. A variety of different replacement fluids may be used.

Conventionally, the operator of the blood processing system will enter the amount of plasma to remove, either by volume or by a fraction of the patient's plasma volume. The amount of replacement fluid added does not necessarily equal the amount of plasma removed. As such, it is typically the case that the amount of replacement fluid used in the TPE is less than the amount that was ordered for the procedure by the operator and connected to the set.

The replacement fluid that is ordered and connected to the set, but not used, cannot be used for another patient. It is considered waste. In addition, while the TPE procedure is of benefit to the patient, a system and method that uses all of the replacement fluid would be better still. That is, it would be better to use all of the replacement fluid, assuming that additional plasma could have been replaced. Consequently, there is room for improvement over existing conventional systems and methods.

SUMMARY

In a first aspect of the disclosure, a processing system includes a processor including a separator, a set configured to cooperate with the separator to separate whole blood into plasma and other components, the set including an inlet line attachable to a patient to receive whole blood and an return line attachable to a patient to return processed fluid, and a source of replacement fluid connected to the disposable set, the processor configured to combine the other components with replacement fluid from the source of replacement fluid to define the processed fluid to be returned to the patient via the return line. The processor includes a controller and an input device coupled to the controller, the controller configured to receive an input via the input device, the input representing a volume of replacement fluid, and to control the processor to separate whole blood passing through the set and to combine the other components with the replacement fluid according to the input until the source of replacement fluid is empty.

In a second aspect of the disclosure, a processing method includes receiving an input representing a volume of replacement fluid in a source, receiving whole blood, separating the whole blood into plasma and other components, combining a replacement fluid with the other components to define a processed fluid, and delivering the processed fluid. The method further includes continuing to separate whole blood, combine the replacement fluid and deliver the processed fluid according to the input until the source is empty.

DETAILED DESCRIPTION

A detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
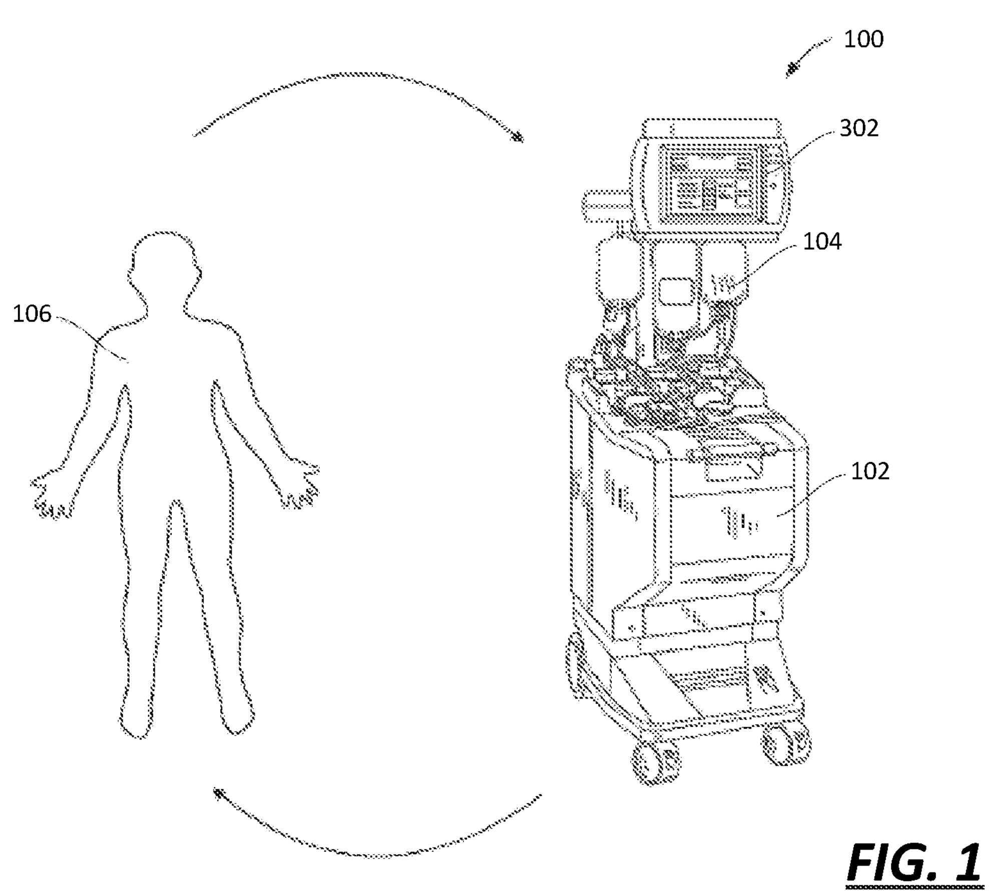
FIG. 1 is a diagram of an embodiment of a processing system including a reusable processor or separator and a disposable processing set or fluid circuit.
Figure 5:
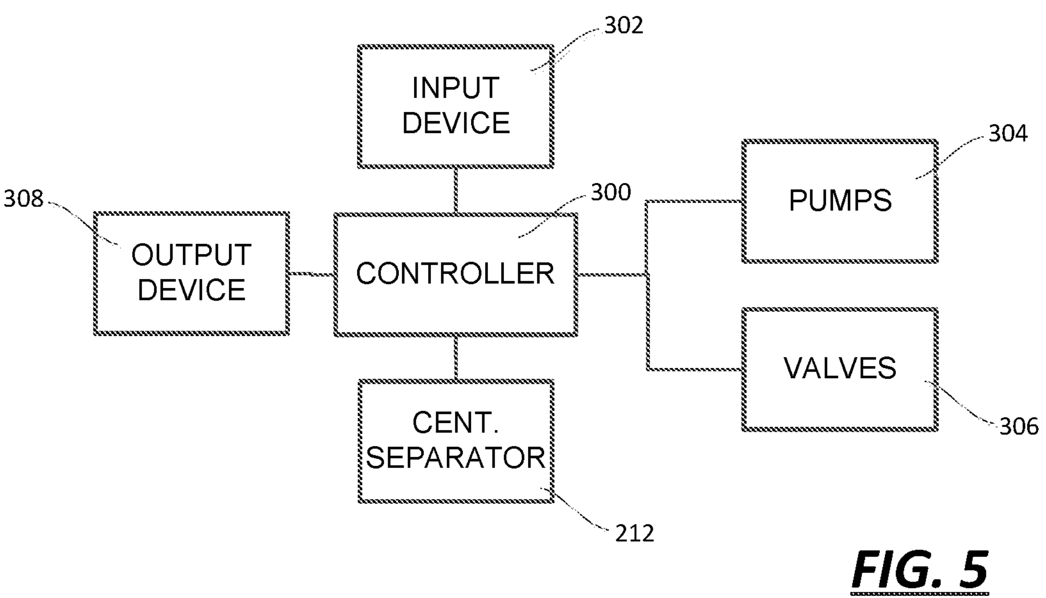
FIG. 5 is a block diagram of the controller of the processing system of FIGS. 1-3, which controller is configured to control the associated equipment to carry out the processing illustrated in FIGS. 4 and 6.

In general terms and with reference to FIGS. 1 and 5, a processing system 100 includes a processor 102 including a separator, a set 104 configured to cooperate with the separator to separate whole blood into plasma and other components, the set 104 including an inlet line attachable to a patient 106 to receive whole blood and an return line attachable to a patient 106 to return processed fluid, and a source of replacement fluid connected to the disposable set 104, the processor 102 configured to combine the other components with replacement fluid to define the processed fluid. The processor 102 includes a controller 300 and an input device 302 coupled to the controller 300, the controller 300 configured to receive an input via the input device 302, the input representing a volume of replacement fluid, and to control the processor 102 to separate whole blood passing through the set and to combine the other components with the replacement fluid according to the input until the source of replacement fluid is empty.

Figure 2:
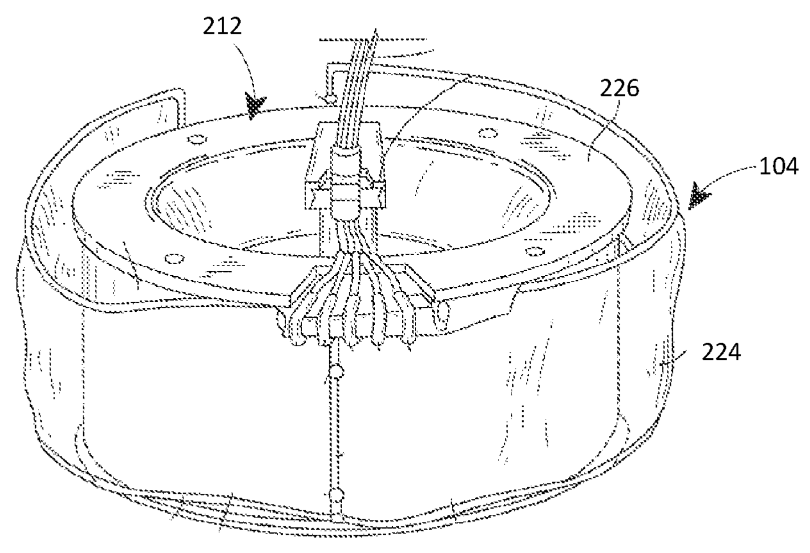
FIG. 2 is a perspective view of a processing container (separation chamber) of a processing set used with the separator of FIG. 1.
Figure 3:
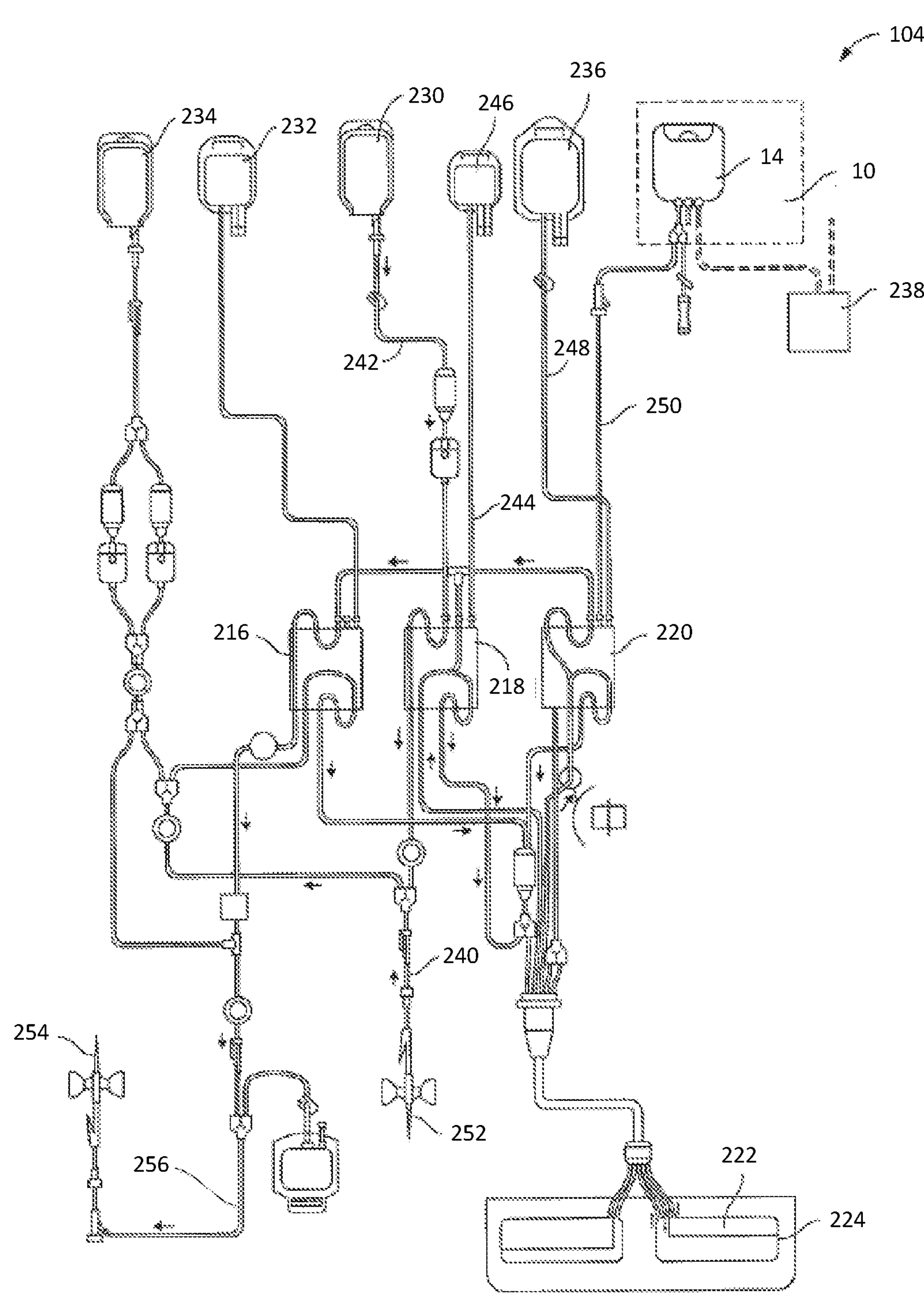
FIG. 3 is a diagram of a processing set for used with the processor of FIG. 1, including the processing container illustrated in FIG. 2.

As to the embodiment of the processor 102 illustrated in FIG. 1, this is an AMICUS® Separator, available from Fresenius Kabi USA, Lake Zurich, Illinois. Briefly, FIGS. 1-3 show the processor 102 in FIG. 1, a representative blood centrifuge 212 (defining part of the processor 102) with a portion of a fluid circuit 104 mounted thereon in FIG. 2, and the entire fluid circuit 104 in FIG. 3. The details of the interaction of such a device 102 and a set 104 are discussed in U.S. Pat. No. 5,868,696, which is incorporated by reference herein in its entirety.

Processing set (also referred to as a fluid circuit) 104 includes a plurality of processing fluid flow cassettes 216, 218, 220 (see FIG. 3) with tubing loops for association with peristaltic pumps on device 102. Set 104 also includes a network of tubing and connected (or pre-connected) containers for establishing flow communication with the patient and for processing and collecting fluids and blood and blood components, as discussed in detail below. The set 104 also includes a separation chamber 222.

As illustrated in FIGS. 2 and 3, the separation chamber 222 is defined by the walls of a flexible processing container 224 carried within an annular gap defined by a rotating spool element 226 (see FIG. 2) and an outer bowl element of the device 102. The processing container 224 takes the form of an elongated tube that is wrapped about the spool element 226 before use. The bowl and spool element 226 are pivoted on a yoke between an upright position and a suspended position. In operation, the centrifuge 212 rotates the suspended bowl and spool element 226 about an axis, creating a centrifugal field within the processing chamber 222 of container 224. Details of the mechanism for causing relative movement of the spool 226 and bowl elements as just described are disclosed in U.S. Pat. No. 5,360,542, the contents of which is also incorporated by reference herein in its entirety.

As seen in FIG. 3, the disposable processing set 104 may include the flexible processing container 224, as well as additional containers, such as a container 230 for supplying anticoagulant, a waste container 232 for collecting waste from one or more steps in a process, a container 234 for holding saline or other wash or resuspension medium, a container 236 for collecting plasma, as well as other containers 238. The set 104 also may include inlet line 240, an anticoagulant (AC) line 242 for delivering AC from container 230, an RBC line 244 for conveying red blood cells from chamber 222 of container 224 to a container 246, a platelet-poor plasma (PPP) line 248 for conveying PPP to container 236 and line 250 for conveying other fluids to and from separation chamber 222 and the containers 238. In addition, the blood processing set 104 includes one or more venipuncture needle(s) for accessing the circulatory system of the patient. As shown in FIG. 2, set 104 includes an inlet needle 252 attached to the inlet line 240 and a return needle 254 attached to a return line 256; in an alternative embodiment, a single needle can serve as both the inlet and outlet needle.

Fluid flow through set 104 is preferably driven, controlled and adjusted by a microprocessor-based controller in cooperation with the valves, pumps, weight scales and sensors of device 102 and set 104, the details of which are described in the previously mentioned U.S. Pat. No. 5,868,696. In a general sense, blood is drawn from the patient via the inlet needle 252 into the inlet line 240, where it passes through one or more of the cassettes 216, 218, 220 and may be processed in the processing chamber 222. The containers 230, 232, 234, 236, 238, 246 are also connected via the cassettes 216, 218, 220 to the processing chamber 222, and fluids may be drawn from or passed to the containers 230, 232, 234, 236, 238, 246 as a consequence of the operation of the cassettes 216, 218, 220 and the chamber 222 (and associated pumps and spool/bowl element). Fluid is returned to the patient along return line 122 via return needle 254.

Figure 4:
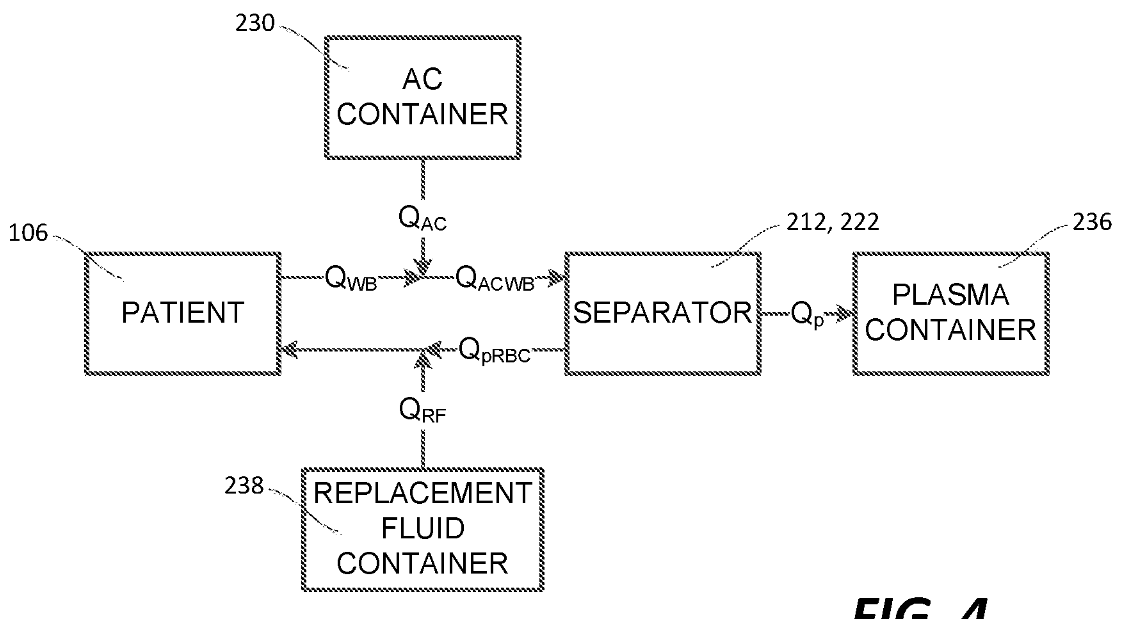
FIG. 4 is a schematic diagram of flows within a processing system, such as the processing system illustrated in FIGS. 1-3, used to perform a therapeutic plasma exchange.

FIG. 4 is a schematic representation of the operation of the processor according to a therapeutic plasma exchange. Whole blood is drawn from the patient (via the needle 252 and line 240, for example), and is combined with anticoagulant from the anticoagulant container 230. The flow rate of the whole blood is represented as $Q_{WB}$, while the flow rate of the anticoagulant is represented as $Q_{AC}$. The flow rate of the combination of the whole blood and the anticoagulant is represented as $Q_{ACWB}$.

The combination of the whole blood and the anticoagulant is introduced into the separator (for example, the centrifugal separator 212 that is configured to receive the processing container 224 that defines the separation chamber 222). The separator operates to separate the plasma from the other components of the whole blood. The plasma is directed to the plasma container 236 at a flow rate represented $Q_P$, while the other components are directed along a separate path at a flow rate designated $Q_{pRBC}$.

Before the other components are delivered or returned to the patient 106, the other components are combined with replacement fluid (for example from the replacement fluid container 238). The replacement fluid is added to the other components at a flow rate represented by $Q_{RF}$. The combination of the other components and the replacement fluid is returned, for example, via the return needle 254 and the return line 256.

Figure 6:
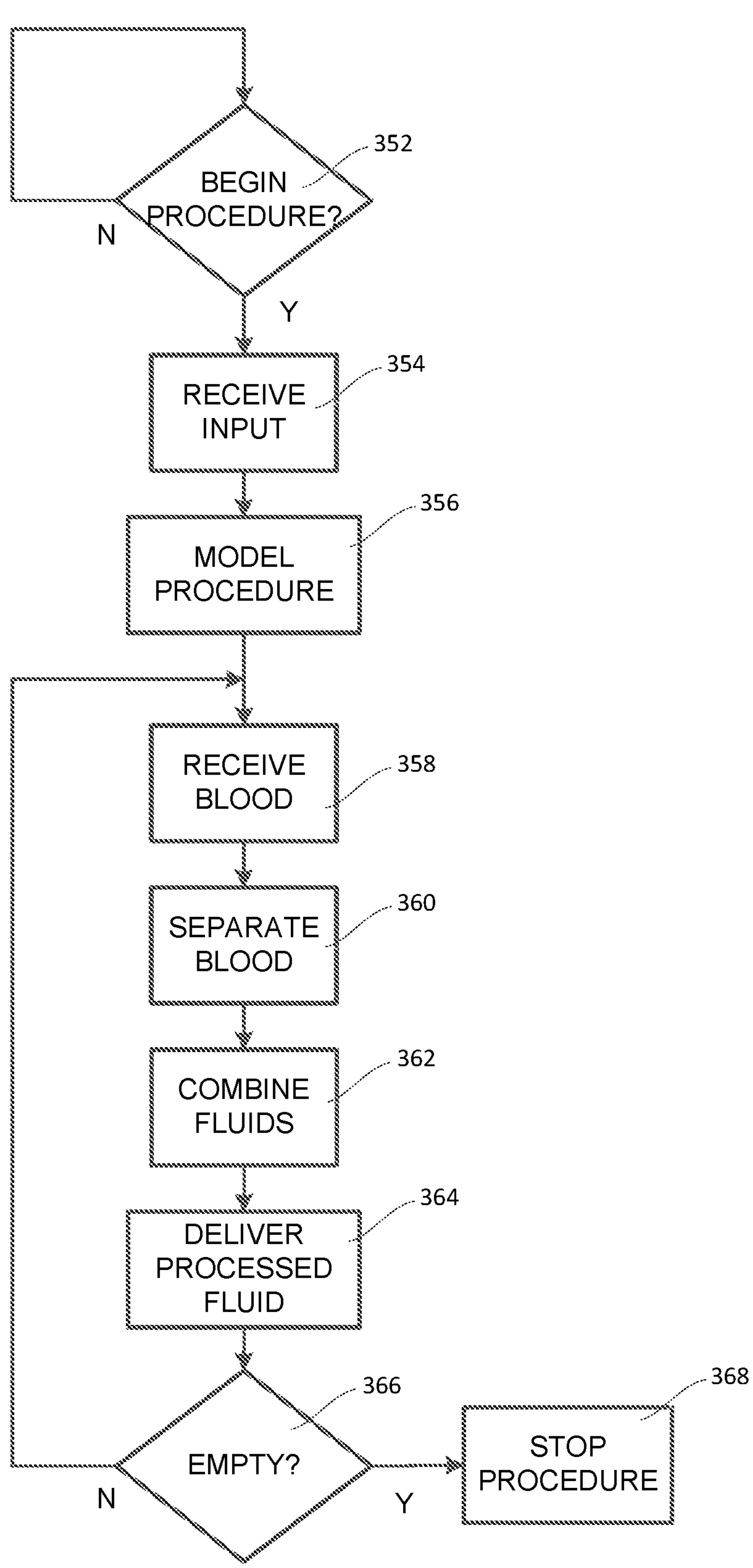
FIG. 6 is a flowchart of a method for using the system of FIGS. 1-3 to perform a therapeutic plasma exchange procedure according to an input representative of a volume of replacement fluid available.

The processor 102 includes a controller 300 (see FIG. 5) that controls the operation of the processor 102 so that the processor 102 operates according to the TPE procedure schematically represented in FIGS. 4 and 6. To that end, the controller 300 may be coupled, via a direct or indirect connection, to an input device 302. The input device 302 is configured to receive an input representative of a volume of replacement fluid available in a replacement fluid container (e.g., the container 238) for a therapeutic plasma exchange procedure. For example, the input device 302 may be a touch screen, as represented in FIG. 1, which touch screen may be associated with a graphical user interface to display requests for inputs to a user, along with an explanation of the format of the input requested. For example, the touch screen may display a region of the screen bounded by a graphical box, in which the user may enter a number representing the volume in the container; alternatively, the user may be able to manipulate a control to raise or lower a number displayed within the box to a value representing the volume in the container.

As illustrated in FIG. 5, the controller 300 may be coupled to the equipment of the processor 102, such as the centrifugal separator 212 mentioned previously, as well as various pumps 304 (e.g., peristaltic pumps) and valves 306 (e.g., pinch valves) that cooperate with the set 104 to move fluid through the set 104 in a selected fashion or pattern to perform a procedure, such as a therapeutic plasma exchange procedure. The controller 300 may also be coupled to an output device 308, such as an electronic video display associated with the input device/touch screen 302, to display information and/or warnings to the user. For example, the controller 300 may control the output device 308 to display an announcement to the user when the replacement fluid container is empty.

The controller 300 may be configured to carry out the therapeutic plasma exchange discussed in general terms above and illustrated in FIG. 4, and in particular the therapeutic plasma exchange procedure illustrated in FIG. 6. To this end, the controller 300 may include a microprocessor (which, in fact may include multiple physical and/or virtual processors). According to other embodiments, the controller 300 may include one or more electrical circuits designed to carry out the actions described herein. In fact, the controller 300 may include a microprocessor and other circuits or circuitry. In addition, the controller 300 may include one or more memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessors to carry out one or more actions as described below.

As mentioned above, a method 350 of operating the processor 102 is illustrated in FIG. 6. The method 350 may be varied, for example as discussed below, according to different embodiments of the method 350. The method 350 begins at block 352, wherein the controller 300 determines if the user desires to begin the procedure. Until the controller 300 determines that the user desires to begin the procedure (e.g., receipt of an input from the input device 302), the method 350 remains at block 352.

When the controller 300 determines that the user desires to begin the procedure, the method 350 passes to block 354, and the controller 300 receives one or more inputs via the input device 302, including an input representing a volume of replacement fluid in a container, such as the container 258. It should be understood that while the container 258 is referred to in the singular for ease of explanation, this description is intended to cover an embodiment of the method 350 wherein the input represents a volume of replacement fluid, which volume may be disposed in more than one container.

Based on the input received at block 354, the controller 300 determines the control of the processor 102 necessary to use all or nearly all of the volume of replacement fluid represented by the input. This determination may be based on a modeling of the procedure wherein the replacement fluid volume is a known, and the plasma to be removed is an unknown to be estimated using the modeling process. The modeling may use certain known parameters in addition to the replacement fluid volume, including the patent's height, weight, gender and hematocrit. Further, the modeling may use the targeted change in the patient's total fluid volume, the targeted anticoagulant ratio, and the targeted maximum citrate infusion rate. In turn, the modeling may estimate, in addition to the estimated volume of pure plasma to be removed, the estimated volume of pure plasma and anticoagulant to be removed, and the number of plasma volumes to be removed. Further, the modeling may estimate the procedure time, the volume of anticoagulant (i) required, (ii) in the plasma, and (iii) returned to the patient, and the flow rates of (i) the whole blood and anticoagulant, (ii) the anticoagulant, (iii) the plasma, (iv) the packed RBC, and (v) the replacement fluid.

According to certain embodiments, the controller 300 controls the processor 102 to carry out the procedure immediately after the modeling is performed. According to other embodiments, the controller 300 may control the output device 308 to display one or more parameters of the procedure to the operator before carrying out the procedure. For example, the controller 300 may control the output device 308 to display the amount of plasma that will be removed and replaced according to the modeling performed. The controller 300 may control the processor 102 to carry out the procedure immediately after the parameter(s) is/are displayed, or the controller 300 may pause the operation of the processor 102 for a given time period or until a further input is received via the input device 302. The controller 300 may even prevent operation of the processor 102 if the amount of plasma to be removed based on the input received via the input device exceeds a predetermined threshold.

To perform the procedure, the method 350 passes to the actions of blocks 358, 360, 362, 364. At block 358, the controller 300 controls the processor 102 to receive blood from the patient. At block 360, the controller 300 controls the processor 102, and in particular the centrifugal separator 212, to separate the blood into a plasma and other components. The controller 300 may also control the processor 102 to direct the plasma into a first container, while directing the other components along a separate path. It is possible that the controller 300 may control the processor 102 to direct certain of the other components to other containers as well. At block 362, the other components flowing along the separate path are combined with the replacement fluid from the replacement fluid source (e.g., a replacement fluid container). At block 364, the combination of the other components and the replacement fluid is delivered to the patient, for example via the return needle 254 and return line 256.

The controller 300 may carry out other actions as part of the actions of blocks 358, 360, 362, 364, or in addition to the actions of blocks 358, 360, 362, 364. For example, the controller 300 may cause the processor 102 to carry out actions to check the proper installation of the set 104 on the processor 102, and to prime the set 104 once the determination is made that the set 104 is properly installed. As a further example, the controller 300 may control the processor 102 to add anticoagulant from an anticoagulant container to the blood received from the patient, which action may be considered to occur as part of the action of block 358. Consequently, the flow chart of FIG. 6 is intended to be illustrative, and not exhaustive.

At block 366, the controller 300 makes a determination whether to stop the procedure. As noted above, the controller 300 is configured to stop the procedure only when the volume of replacement fluid has been used, which may also be referred to as when the container of replacement fluid is empty. As noted above, this determination is based, at least, on the modeling of the procedure to determine an estimated volume of the patient's plasma to be removed before the procedure is begun. According to other embodiments, modeling of the procedure may be conducted not only before the procedure has begun, but also during the procedure. As a consequence, the determination to stop the procedure may be based on an estimate of the total plasma to be removed, based on the total volume of replacement fluid represented by the input received via the input device 302, or the determination may be based on estimates of the total plasma to be removed calculated during the procedure. In any event, when the controller 300 makes the determination that the replacement fluid is empty, the method 350 passes to block 368.

It the determination is made at block 366 that the container is empty, then the procedure stops at block 368. If the determination is made at block 366 that the container is not empty (for example, according to those embodiments where the determination is based on modeling of the procedure occurring during the procedure), then the method 350 may returns to block 358 and repeats blocks 358, 360, 362, 364 according to the illustrated embodiment.

The modeling performed at block 356 is now discussed with reference to several equations. Some of these equations are used to calculate parameters considered to be known parameters from measured values, such as height, weight and hematocrit. Some of these equations are used to model the procedure to determine the estimates for the parameters mentioned above. These equations refer, in part, to the schematic of the system illustrated in FIG. 4.

Initially, the controller 300 may receive information regarding the patient's height, weight, and gender, which information may be received via the input device 302. From this information, an initial calculation of the patient's total blood volume, $V_0$, may be performed using, for example, the Nadler equations. There are two different equations, a first for males ($V_{0,male}$) and a second for females ($V_{0,female}$):

$$V_{0,male}=1000\times(0.3669\times h^3+0.3219\times w+0.6041) \quad \text{[Eqn. 1a]}$$

$$V_{0,female}=1000\times(0.3561\times h^3+0.3308\times w+0.1833) \quad \text{[Eqn. 1b]}$$

where $V_0$ is the total blood volume (for males or females) in milliliters, h is height in meters, and w is weight in kilograms. Alternatively, the patient's total blood volume may be provided directly.

The information regarding the patient's total blood volume may be combined with the patient's hematocrit to calculate the patient's total initial plasma volume:

$$TPV_0=V_0\times(1-H_0) \quad \text{[Eqn. 2]}$$

where $TPV_0$ is the total initial plasma volume, $V_0$ is the total initial blood volume (which may be calculated using the Nadler equations, above), and $H_0$ is the initial hematocrit (which is a known parameter).

As to the parameters required to be estimated, one may derive the equation used to estimate the replacement fluid flow rate, $Q_{RF}$, in the following fashion. The procedure time is related to two targeted endpoints, the time to deplete the replacement volume and the time to reach a desired change to patient's total volume. The time to deplete the replacement volume may be expressed as:

$$t_{RF} = \frac{V_{RF}}{Q_{RF}} \quad \text{[Eqn. 3]}$$

where $t_{RF}$ is the time to deplete the replacement volume, $V_{RF}$ is the volume of replacement fluid to be depleted (which is a known parameter), and $Q_{RF}$ is the flow rate of the replacement fluid. The time it takes to reach final fluid balance may be expressed as:

$$t_{VF} = \frac{\Delta V}{Q_{pRBC} + Q_{RF} - (Q_{ACWB} - Q_{AC})} \quad \text{[Eqn. 4]}$$

Where $t_{VF}$ is the time to reach the final fluid balance, $\Delta V$ is the change in patient's volume (considered to be a known parameter), and the flow rates are as explained above relative to FIG. 4.

By equating the equation for calculating the time to deplete the replacement fluid (Eqn. 3) with the equation for calculating the time to reach final fluid balance (Eqn. 4), a further equation of assistance in estimating the other parameters of the TPE procedure may be derived. That is, $$\frac{V_{RF}}{Q_{RF}} = \frac{\Delta V}{Q_{pRBC} + Q_{RF} - (Q_{ACWB} - Q_{AC})}$$

It will be recognized from FIG. 4 that $Q_{pRBC}=Q_{ACWB}-Q_p$, and thus the above equation may be expressed as:

$$[-Q_p + Q_{AC}] = \frac{(\Delta V - V_{RF})}{V_{RF}} \times Q_{RF}$$

Solving for the flow rate of the replacement fluid, $Q_{RF}$, yields:

$$Q_{RF} = \frac{V_{RF}}{(V_{RF} - \Delta V)}[Q_P - Q_{AC}] \quad \text{[Eqn. 5]}$$

Thus, if the patient's total blood volume is to remain constant, the rate of replacement fluid delivery is exactly equal to the rate of plasma removal less the rate of anticoagulant addition. Any volume change of the patient would require the rate of replacement fluid delivery to be slightly higher for an increase in patient's blood volume, or lower for a decrease in patient's blood volume.

As to the remaining equations that may be useful in estimating the flow rates, the following are provided as examples.

The anticoagulant flow rate may be estimated using:

$$Q_{AC} = \frac{Q_{ACWB}}{(\mathrm{AC}+1)}$$

where AC is the targeted anticoagulant ratio.

The plasma flow rate may be estimated using:

$$Q_P = Q_{ACWB} \times \left(1 - \frac{H_{ACWB}}{H_pRBC}\right)$$

where the prime adjusted hematocrit is defined as:

$$H_{ACWB} = H_{0,adj} \times \left(\frac{\mathrm{AC}}{\mathrm{AC}+1}\right)$$

where the diluted hematocrit is defined as:

$$H_{0,adj} = \frac{H_0 + V_0}{V_0 + ECV}$$

with ECV being the extracorporeal volume of the set or circuit, and the packed RBC hematocrit is defined as:

$$H_{pRBC} = 0.963 - \frac{54858 H_{ACWB} Q_{ACWB}}{\omega^2}$$

where ω=2*centrifuge speed.

The whole blood flow rate may be estimated using:

$$Q_{ACWB,max} = \frac{CIR_{LIM}}{CIR_{c,RF} \times RR\left(1 - \frac{H_{ACWB}}{H_{pRBC}}\right) + C_{c,AC} \times \text{Plasma AC Fraction}(1 - H_{pRBC})\left(\frac{H_{ACWB}}{H_{pRBC}}\right)}$$

where $CIR_{C,RF}$ is the citrate concentration in the replacement fluid, $C_{c,AC}$ is the citrate concentration in the anticoagulant, the return ratio (RR) is defined as:

$$RR = \frac{Q_{RF}}{Q_P}$$

and the Plasma AC Fraction is defined as:

$$\text{Plasma AC Fraction} = \frac{1}{(1 - H_{0,adj}) \times \text{AC} + 1}$$

The anticoagulant in the waste plasma is defined as:

$$V_{AC,plasma} = \frac{V_P}{\left[\left(\frac{1}{\text{Plasma AC Fraction}}\right) - 1\right]}$$

where $V_p$ (volume of patient's pure plasma to be removed) is defined as:

$$V_P = V_{RF} + V_{AC,pat}$$

where $V_{AC,pat}$ (volume of anticoagulant returned to patient) is defined as:

$$V_{AC,pat} = V_{AC,req} - V_{AC,plasma}$$

where $V_{AC,req}$ is the volume of anticoagulant required for the procedure. Further, $V_{p,tot}$ (volume of patient's pure plasma plus anticoagulant volume) may be defined as:

$$V_{P,tot} = V_P + V_{AC,plasma}$$

and $N_{PV}$ (number of plasma volumes) is defined as:

$$N_{PV} = \frac{V_P}{TPV_0}$$

Thus, an improved method and system for carrying out a procedure involving use of a replacement fluid, such as a TPE procedure, has been disclosed. The description provided above is intended for illustrative purposes, and is not intended to limit the scope of the disclosure to any particular method, system, apparatus or device described herein.

Other Aspects

Aspect 1. A processing system comprising:

a processor comprising a separator;

a set configured to cooperate with the separator to separate whole blood passing through the set into plasma and other components, the set comprising an inlet line attachable to a patient to receive whole blood from the patient and a return line attachable to a patient to return processed fluid to the patient; and a source of replacement fluid connected to the disposable set, the processor configured to combine the other components with replacement fluid from the source of replacement fluid to define the processed fluid returned to the patient via the return line, wherein the processor comprises a controller and an input device coupled to the controller, the controller configured to receive an input via the input device, the input representing a volume of replacement fluid, and to control the processor to separate whole blood passing through the set and to combine the other components with the replacement fluid according to the input until the source of replacement fluid is empty.

Aspect 2. The processing system according to aspect 1, wherein the controller is configured to calculate an amount of plasma to be removed based on the input received via the input device, and to control the processor to separate whole blood passing through the set and to combine the other components with the replacement fluid until the amount of plasma to be removed has been achieved.

Aspect 3. The processing system according to aspect 1, wherein the controller controls the processor to combine the other components with the replacement fluid according to a replacement fluid flow rate, Qrf, according to the following equation:

$$Q_{RF} = \frac{V_{RF}}{(V_{RF} - \Delta V)}[Q_P - Q_{AC}]$$

where Vrf=volume of replacement fluid according to the input received via the input device;

ΔV=targeted change in the patient's total blood volume;

Qp=flow rate of plasma; and

Qac=flow rate of anticoagulant.

Aspect 4. The processing system according to aspect 1, wherein the separator comprises a centrifugal separator, and the set comprises a processing container defining a separation chamber, the processing container received within the centrifugal separator.

Aspect 5. The processing system according to aspect 1, the separator having an inlet port, and further comprising a source of anticoagulant coupled to the inlet line between the patient and the inlet port of the separator.

Aspect 6. A processing method comprising:

receiving an input representing a volume of replacement fluid in a source;

receiving whole blood;

separating the whole blood into plasma and other components;

combining a replacement fluid with the other components to define a processed fluid;

delivering the processed fluid; and continuing to separate whole blood, combine the replacement fluid and deliver the processed fluid according to the input until the source is empty.

Aspect 7. The processing method according to aspect 6, further comprising calculating an amount of plasma to be removed based on the input received via the input device, and continuing to separate whole blood passing through the set and to combine the other components with the replacement fluid until the amount of plasma to be removed has been achieved.

Aspect 8. The processing method according to aspect 6, wherein the replacement fluid is combined with the other components according to a replacement fluid flow rate, Qrf, according to the following equation:

$$Q_{RF} = \frac{V_{RF}}{(V_{RF} - \Delta V)}[Q_P - Q_{AC}]$$

where Vrf=volume of replacement fluid according to the input

ΔV=targeted change in the patient's total blood volume

Qp=flow rate of plasma

Qac=flow rate of anticoagulant.

Aspect 9. The processing method according to aspect 6, wherein separating the whole blood into plasma and other components comprises centrifuging the whole blood.

The invention claimed is:

1. A blood processing system comprising:

a separator;

a disposable set configured to cooperate with the separator to separate whole blood passing through the disposable set into plasma and other components, the disposable set attachable to a person to receive the whole blood from the person and to return the other components to the person, the disposable set configured to receive replacement fluid from a source of replacement fluid and to deliver the replacement fluid to the person;

a control circuit; and an input device comprising a touch screen coupled to the control circuit, the control circuit configured to receive an input via the input device, the input representing a volume of replacement fluid, wherein the touch screen displays a region of the screen bounded by a graphical box and a control to raise or lower a number displayed within the graphical box, the number being the input representing the volume of replacement fluid, wherein the control circuit is further configured to calculate an amount of plasma to be removed based on the person's height, weight, hematocrit, and the input representing the volume of replacement fluid and to control the separator to separate whole blood passing through the disposable set and to deliver the replacement fluid until the amount of plasma to be removed has been achieved.

2. The blood processing system of claim 1, wherein the control circuit is configured to operate the touch screen to display an announcement to the user when the replacement fluid container is empty.

3. The blood processing system of claim 1, wherein the control circuit is configured to operate the touch screen to display the amount of plasma to be removed to an operator before carrying out the procedure.

4. The blood processing system of claim 3, wherein the control circuit is configured to pause the processing until a further input is received via the input device.

5. The blood processing system of claim 1, wherein the control circuit is configured to operate the touch screen to display the volume of replacement fluid.

6. The blood processing system of claim 1, wherein the control circuit is configured to calculate the amount of plasma to be removed using the weight and height to calculate total blood volume of the person and the hematocrit to calculate the total plasma volume of the person.

7. The blood processing system of claim 1, wherein the control circuit is configured to deliver the replacement fluid until a volume of replacement fluid delivered equals the volume of replacement fluid displayed in the graphical box.

8. The blood processing system of claim 7, wherein the replacement fluid is delivered until the control circuit makes the determination that the replacement fluid source is empty.

9. The blood processing system of claim 1, wherein the blood processing system is configured to repeat the receiving of whole blood, separation of whole blood passing through the disposable set and delivering the replacement fluid until the amount of plasma to be removed has been achieved for the person.

10. The blood processing system of claim 9, wherein the replacement fluid is delivered at the end of each iteration of the receiving and separation.

11. The blood processing system of claim 1, wherein the number displayed in the graphical box represents a volume of replacement fluid available in a replacement fluid container.

12. A blood processing system comprising:

a separator;

a disposable set configured to cooperate with the separator to separate whole blood passing through the disposable set into plasma and other components, the disposable set attachable to a person to receive whole blood from the person and to return the other components to the person, the disposable set configured to receive replacement fluid from a source of replacement fluid and to deliver the replacement fluid to the person;

a control circuit; and an input device comprising a touch screen coupled to the control circuit, the control circuit configured to receive an input via the input device, the input representing a volume of replacement fluid, wherein the touch screen displays a region of the screen bounded by a graphical box and a number displayed within the graphical box, the number being the input representing the volume of replacement fluid, wherein the control circuit is further configured to calculate an amount of plasma to be removed based on the person's height, weight, hematocrit, and the input representing the volume of replacement fluid, wherein the control circuit is configured to calculate the amount of plasma to be removed using the weight and height to calculate total blood volume of the person and the hematocrit to calculate the total plasma volume of the person, wherein the control circuit is further configured to control the separator to receive whole blood from the person, separate the whole blood passing through the disposable set, return the other components to the person and deliver the replacement fluid until the amount of plasma to be removed has been achieved.

13. The blood processing system of claim 12, wherein the control circuit is further configured to deliver the volume of replacement fluid represented by the number displayed in the graphical box.

14. The blood processing system of claim 13, wherein the number displayed in the graphical box represents a volume of replacement fluid available in a replacement fluid container.

15. The blood processing system of claim 12, wherein the control circuit is configured to operate the touch screen to display the amount of plasma to be removed to an operator before carrying out the procedure.

16. The blood processing system of claim 12, wherein the control circuit is further configured to repeat for another iteration controlling the separator to receive whole blood from the person, separate whole blood passing through the disposable set, return the other components to the person and deliver the replacement fluid, wherein replacement fluid is delivered at each iteration.

* * * * *